United States Patent [19]

Cho

[11] Patent Number: 5,549,600
[45] Date of Patent: Aug. 27, 1996

[54] SURGICAL LASER PROBE WITH THERMAL CUTTING

[75] Inventor: George Cho, Hopkinton, Mass.

[73] Assignee: Cynosure, Inc., Bedford, Mass.

[21] Appl. No.: 270,032

[22] Filed: Jul. 1, 1994

[51] Int. Cl.$^6$ .................................................. A61B 17/36
[52] U.S. Cl. ........................... 606/15; 606/7; 606/16; 606/28
[58] Field of Search ................... 606/27, 28, 2, 606/3, 7, 13–16

[56] References Cited

U.S. PATENT DOCUMENTS

| | | |
|---|---|---|
| 3,821,510 | 6/1974 | Muncheryan . |
| 3,843,865 | 10/1974 | Nath . |
| 3,858,577 | 1/1975 | Bass et al. . |
| 4,233,493 | 11/1980 | Nath . |
| 4,273,109 | 6/1981 | Enderby . |
| 4,313,431 | 2/1982 | Frank . |
| 4,539,987 | 9/1985 | Nath et al. . |
| 4,592,353 | 6/1986 | Daikuzono . |
| 4,662,368 | 5/1987 | Hussein et al. . |
| 4,693,244 | 9/1987 | Daikuzono . |
| 4,693,556 | 9/1987 | McCaughan, Jr. ................ 606/15 X |
| 4,735,201 | 4/1988 | O'Reilly ................................ 606/28 |
| 4,736,743 | 4/1988 | Daikuzono . |
| 4,890,898 | 1/1990 | Bentley et al. ...................... 606/15 |
| 4,913,142 | 4/1990 | Kittrell et al. ........................ 606/7 |
| 4,968,314 | 11/1990 | Michaels ........................ 606/15 X |
| 5,209,748 | 5/1993 | Daikuzono ..................... 606/15 X |
| 5,300,063 | 4/1994 | Tano et al. ........................... 606/15 |
| B1 4,592,353 | 4/1989 | Daikuzono . |

FOREIGN PATENT DOCUMENTS 2826383 12/1979 Germany .................................. 606/15

Primary Examiner—Angela D. Sykes
Assistant Examiner—Michael Peffley
Attorney, Agent, or Firm—Hamilton, Brook, Smith, & Reynolds, P.C.

[57] ABSTRACT

In an apparatus and method for thermal cutting with a surgical laser probe, fiber optics convey laser light from a source to the surgery region. The laser beam is directed towards tissue for vaporizing the tissue. A bulbous tip member is coupled to the output end of the fiber optics. Vaporization of the tissue by the laser generates charred tissue particulates which naturally collect on the face of the bulbous tip member. The collected charred tissue absorbs reflected light energy from the laser vaporization of tissue. The absorbed energy heats the tip member which causes vaporization of proximate tissue.

20 Claims, 5 Drawing Sheets

SURGICAL LASER PROBE WITH THERMAL CUTTING

BACKGROUND OF THE INVENTION

Endoscopic surgery is often used to perform prostate, intra-uterine, bladder, and urinary tract surgery. The most common method of performing prostate surgery is to resect the enlarged prostate gland with an electrosurgical loop inserted into the urethra through an endoscope. The electrosurgical device shaves off small pieces of prostate tissue in order to enlarge the passageway thereby providing the patient with relief. A problem with this method of surgery is that substantial bleeding occurs as the prostate tissue is cut, making visibility through the endoscope difficult. Blood loss also complicates the surgical operation and lengthens the hospital stay. This method of surgery is lengthy and difficult to perform and requires extensive training.

In another method, fiber optics are inserted into the prostate gland through an endoscope. Divergent laser energy conveyed by the optical fiber coagulates surrounding prostate gland tissue. The coagulated tissue remains in place for about 4 to 6 weeks before passing during urination. Therefore, the patient must endure a long period of discomfort and may need a catheter to assist urine passage until the coagulated tissue passes.

Another method employs thermal cauterization using a probe with a hot metal tip. Fiber optics are inserted into the prostate gland through an endoscope. Laser energy is supplied for heating a metal tip located on the end of the fiber optics. Tissue within proximity to the metal tip is cauterized. A disadvantage of this method is its inaccuracy.

SUMMARY OF THE INVENTION

The present invention relates to an apparatus and method for thermal cutting with a surgical laser probe. The apparatus of the invention includes fiber optics, a laser light source, and a bulbous tip member. The laser light source is optically coupled to the input end of the fiber optics. The fiber optics convey laser light from the light source to the output end of the fiber optics. The laser beam is directed towards tissue for vaporizing the tissue. The bulbous tip member is coupled to the output end of the fiber optics. Charred tissue vaporized by the laser beam collects on the tip member, which absorbs heat energy from reflected laser light, causing the tip member to heat up. Heat radiated by the tip member vaporizes tissue proximate to the tip member.

The bulbous tip may be continuous across its face or may have a hole for communicating with the fiber optics. The bulbous tip may include an extension on its face for communicating with fiber optics. In the case where the tip is continuous across its face, it is preferred that the bulbous tip comprise material which is transparent to light at the laser wavelength. The face of the bulbous tip may include a hole for communicating with the fiber optics. The diameter of the fiber optics may be substantially similar to the diameter of the hole providing a snug fit for securing the fiber optics in the hole. The fiber optics may be secured in the hole by fusing the fiber optics to the bulbous tip. The bulbous tip may be substantially solid having a hole along its length for communicating with the fiber optics.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
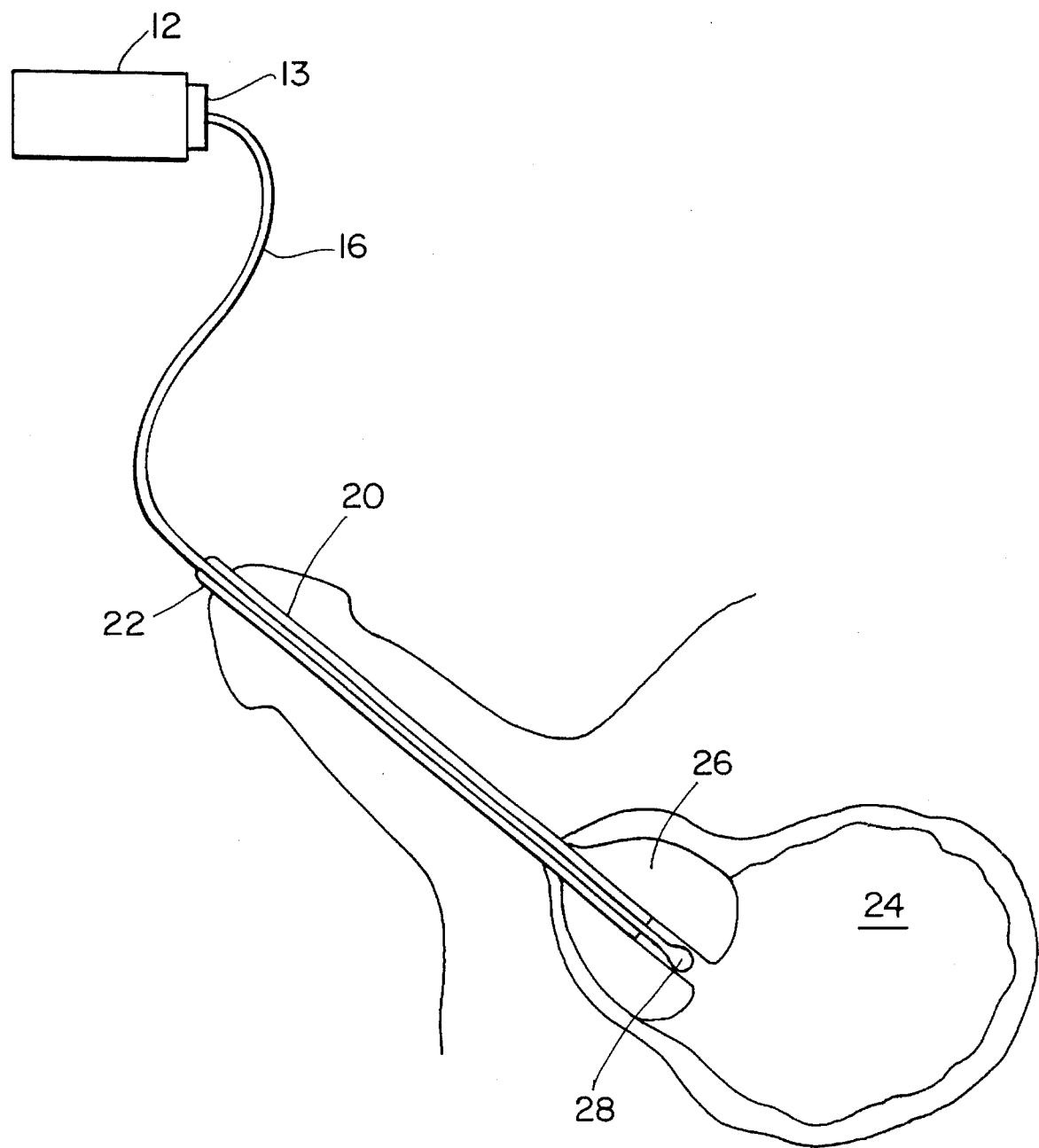
FIG. 1 is a sectional side illustration of a surgical laser probe used for prostate surgery in accordance with the present invention.

FIG. 1 is a sectional side illustration of a surgical laser probe with thermal cutting used for performing prostate surgery. The probe includes a laser light source 12 coupled to the input end of fiber optics 16 at connector 13. Connector 13 is of the low profile type described in U.S. patent application Ser. No. 08/242,308 incorporated herein by reference. The fiber optics 16 pass through an endoscopic sheath 22. The endoscopic sheath 22 includes viewing optics (not shown) for enabling a surgeon to view surgical areas. A light delivery tip 28 is coupled to the output end of the fiber optics 16. The surgeon, using the viewing optics, guides the light delivery tip 28 into regions of the prostate 26 to be excised.

Figure 2:
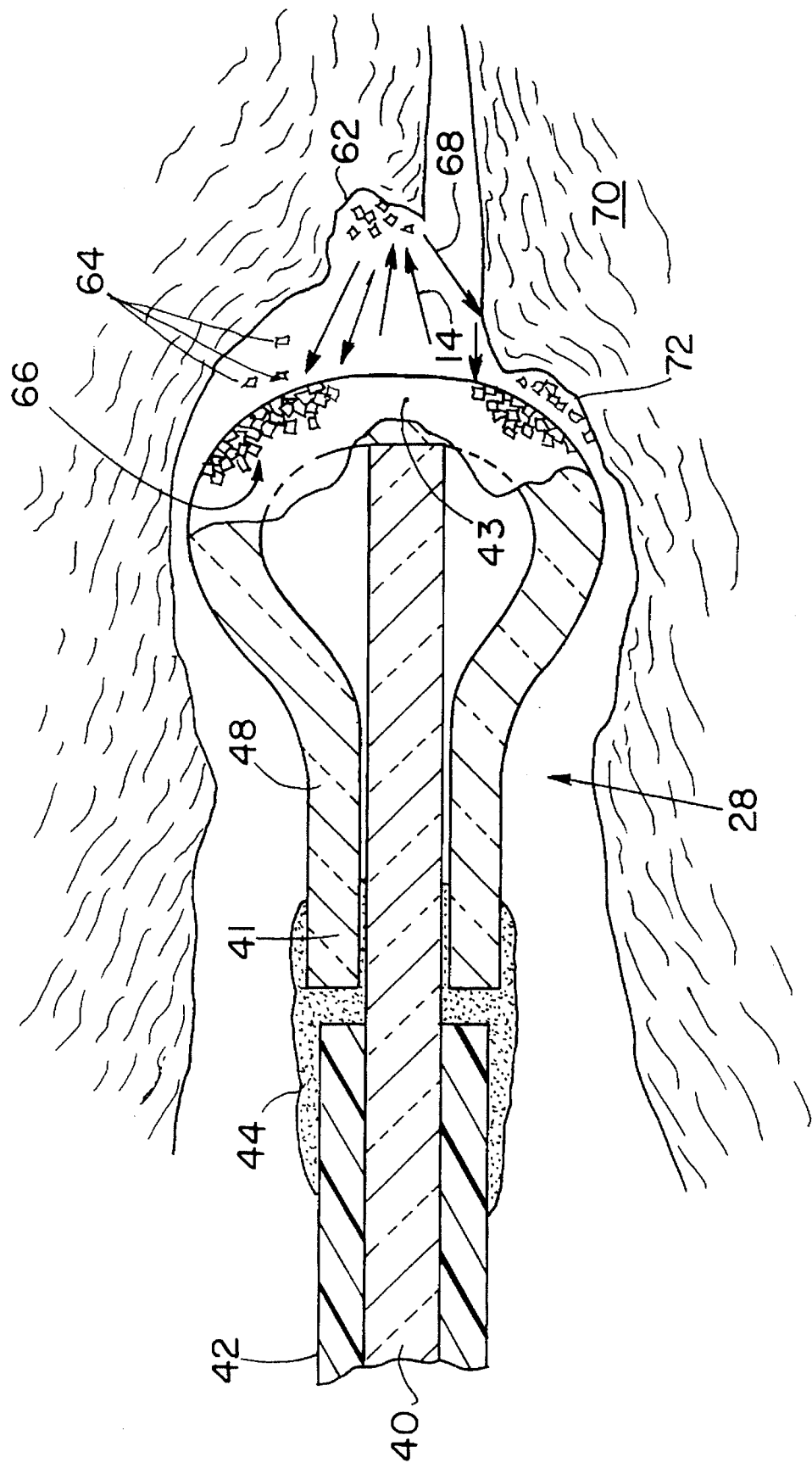
FIG. 2 is a close-up sectional side view of a light delivery tip vaporizing tissue thermally and with laser light in accordance with the present invention.

FIG. 2 is a close-up sectional side view of a light delivery tip 28 excising tissue 70 from the prostate. The surgeon guides the light delivery tip 28 into a region of the prostate where tissue 70 is to be excised. Upon positioning the light delivery tip 28, which includes a bulbous tip member 48, the surgeon projects a beam of laser light through the fiber optics 40 which radiates 14 at the tissue vaporization site 62. The tissue 70 is vaporized into charred particulates 64 which by natural process collect 66 on the front face 43 of the bulbous tip member 48. The charred particulates 64 are residual carbon from tissue following removal of $H_2O$ and $CO_2$ through vaporization. The collection of charred tissue 66 is black in color and therefore absorbs heat energy from reflected laser light 68. The bulbous tip member 48 is hottest at its front face 43, where most laser energy is absorbed and coolest at its rear face 41. The heating of the bulbous tip member 48 causes further vaporization of tissue 72 in regions adjacent the bulbous tip member 48. Therefore, tissue 70 is vaporized both by the laser beam energy 14 and by the thermal energy absorbed by the charred particulates 66 and radiated by the bulbous tip member 48.

The output end of the fiber optics 40 is preferably within approximately 4 mm of the front face 43 of the tip 48, for providing high power density laser energy 14 at the tissue vaporization site 62. The laser beam 14 gives quick, efficient vaporization of tissue while permitting the surgeon to direct the fiber optics 40 closer to the tissue. In this way, the power density is high in the region of vaporization, and is low in nearby regions.

FIGS. 3–6 are sectional side views of various embodiments of light delivery tips in accordance with the present invention. In each embodiment, the fiber optics 40 includes a reflective cladding layer (not shown) for directing the beam longitudinally and for reducing leakage. The fiber optics 40 also includes a buffer sleeve 42 for protecting the fiber optics 40 from breakage and scratching. The buffer sleeve 42 is stripped at the output end of the fiber optics 40. A bulbous tip member 46, 48, 52, 56 is fitted over the exposed area of the fiber optics 40 and secured to the fiber optics 40 with epoxy 44. By coupling the fiber optics 40 to the inside of the bulbous tip 46, 48, 52, 56, a strong bond is given. An intense, highly concentrated beam of laser light 14 is emitted from the output end of the fiber optics 40.

Figure 3:
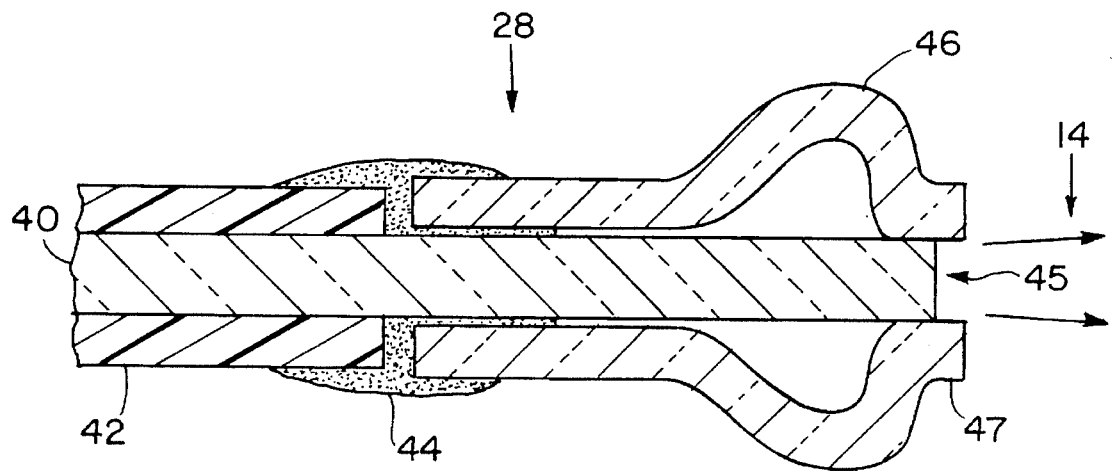
FIG. 3 is a sectional side view of a light delivery tip having a hole and an extension in its front face for communicating with the fiber optics in accordance with the present invention.

In FIG. 3 the bulbous tip 46 has an extension 47 on its front face. The front face of the bulbous tip 46 includes a hole 45 for allowing laser light 14 to pass therethrough. The hole 45 is substantially similar in diameter to the outer diameter of the fiber optics 40 and thus, the fiber optics 40 fits snugly in the hole 45 and communicates with the extension 47. The snug fit secures the bulbous tip 46 in place. The extension 47 simplifies the process of aligning the fiber optics 40 within the bulbous tip. The fiber optics 40 is recessed slightly within the hole 45 so that contact with tissue is avoided. The recession of the fiber optics 40 within the hole 45 is slight, so as not to cause substantial divergence of the laser beam 14. The snug fit also protects the cladding of the exposed fiber within the bulbous tip 46 from damage which would cause further beam divergence. Any leakage of energy from the fiber optics 40 within the bulbous tip 46 gets absorbed by the charred tissue, heating the bulbous tip.

Figure 4:
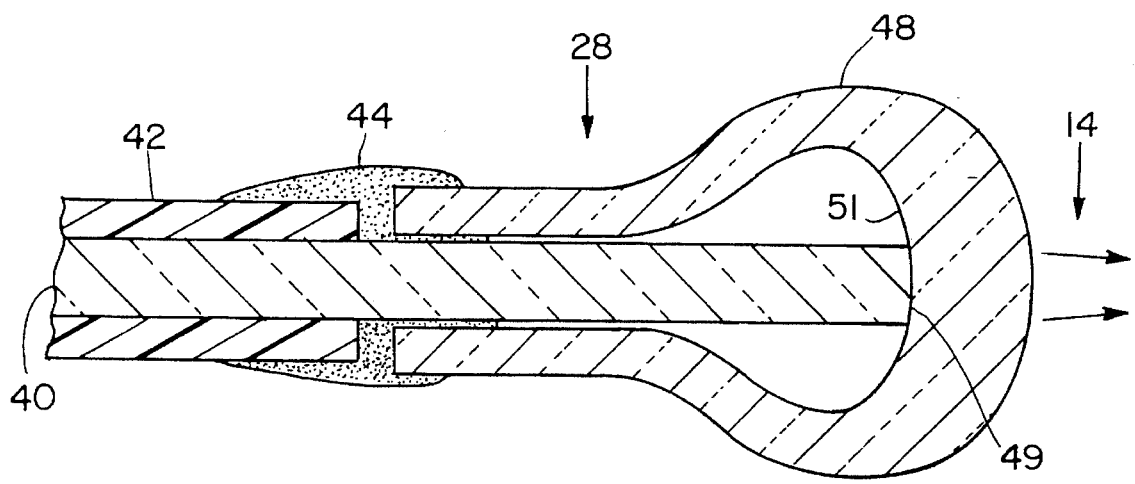
FIG. 4 is a sectional side view of a light delivery tip having a continuous front face in accordance with the present invention.

In FIG. 4 the bulbous tip 48 is continuous on its face and is transparent to light at the laser source wavelength. The output end of the fiber optics 40 is butt-coupled 49 to the inner wall 51 of the front face of the bulbous tip 48. In an embodiment wherein the fiber optics 40 is not butt-coupled 49 to the inner wall 51, the output end of the fiber optics 40 is preferably within 4 millimeters of the front face of the bulbous tip 48, permitting close, efficient vaporization of tissue.

Figure 5:
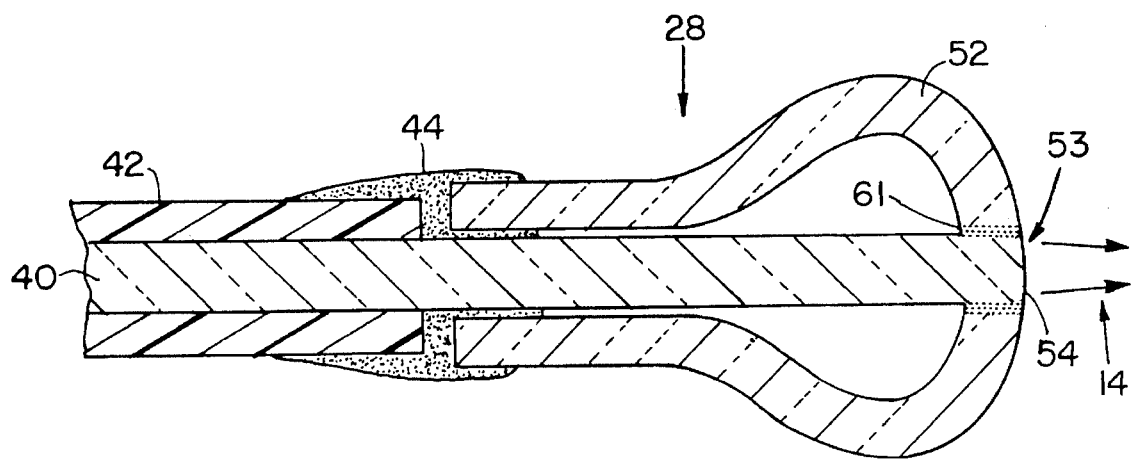
FIG. 5 is a sectional side view of a light delivery tip wherein the fiber optics is fused at its output end in accordance with the present invention.

In FIG. 5, the bulbous tip 52 is similar in shape to the bulbous tip 48 of FIG. 4. However, the tip 52 of FIG. 5 includes a hole 53 on its front face. The hole 53 allows the fiber optics 40 to pass therethrough. The output end of the fiber optics 40 is fused 54, coupling 61 the fiber optics 40 to the bulbous tip 52 around the perimeter of the fiber optics 40, protecting the exposed region of the fiber optics within the cavity of the bulbous tip from charred particulates and from reflected laser energy. Prior art included a ball fused to the end of fiber optics for diverging the laser beam. However, in such embodiments, initiation was slow and mere coagulation resulted rather than cutting or vaporization of the tissue. The present invention immediately vaporizes the tissue with a high power density beam and is much quicker in cutting larger areas with the heating action of the bulb.

Figure 6:
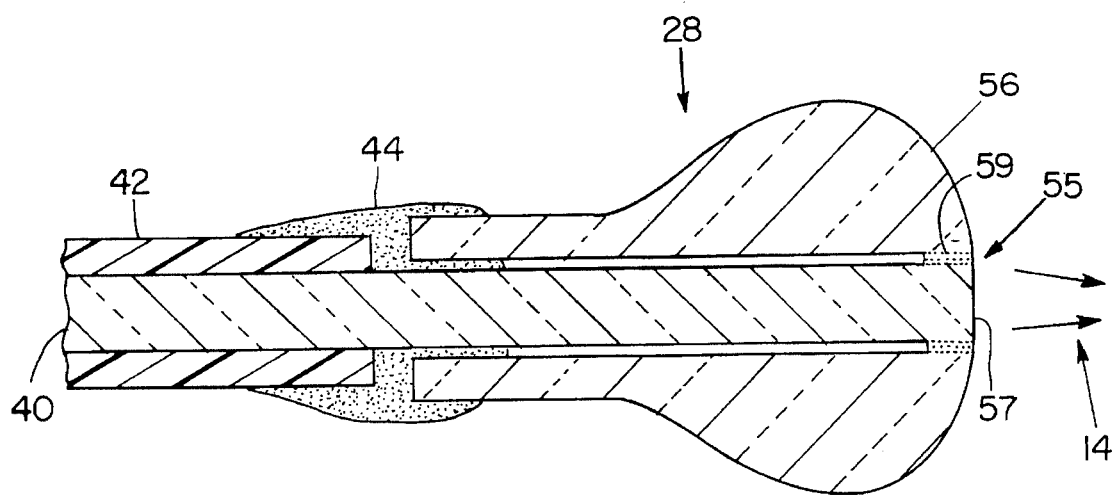
FIG. 6 is a sectional side view of a light delivery tip wherein the fiber optics is fused at its output end and the tip is solid in accordance with the present invention.

In FIG. 6, the bulbous tip 56 is substantially solid in comparison to the embodiments of FIGS. 3, 4 and 5. The bulbous tip 56 includes a hole 55, allowing the fiber optics 40 to be seated therein. The output end of the fiber optics 40 is positioned to align with the front face of the bulbous tip 56 and is fused 57. The fusion couples 59 the fiber optics 40 to the bulbous tip 56 around the perimeter of the fiber optics 40. Alternatively, the fiber optics 40 may be secured in the hole 55 with a snug fit, similar to the embodiment of FIG. 3. In this embodiment, the diameter of the hole 56 is substantially similar to the diameter of the fiber optics 55. The snug fit secures the fiber optics in the hole without the need for fusion.

In the embodiments of FIG. 5 and FIG. 6, the cladding proximate to the output end of the fiber optics is preferably removed before fusing the fiber optics 40 to the bulbous tip 52. The cladding layer commonly comprises a plastic material which cannot withstand the preferred 1,000° C. fusion temperature of the silica fiber optics and silica bulb.

Figure 7:
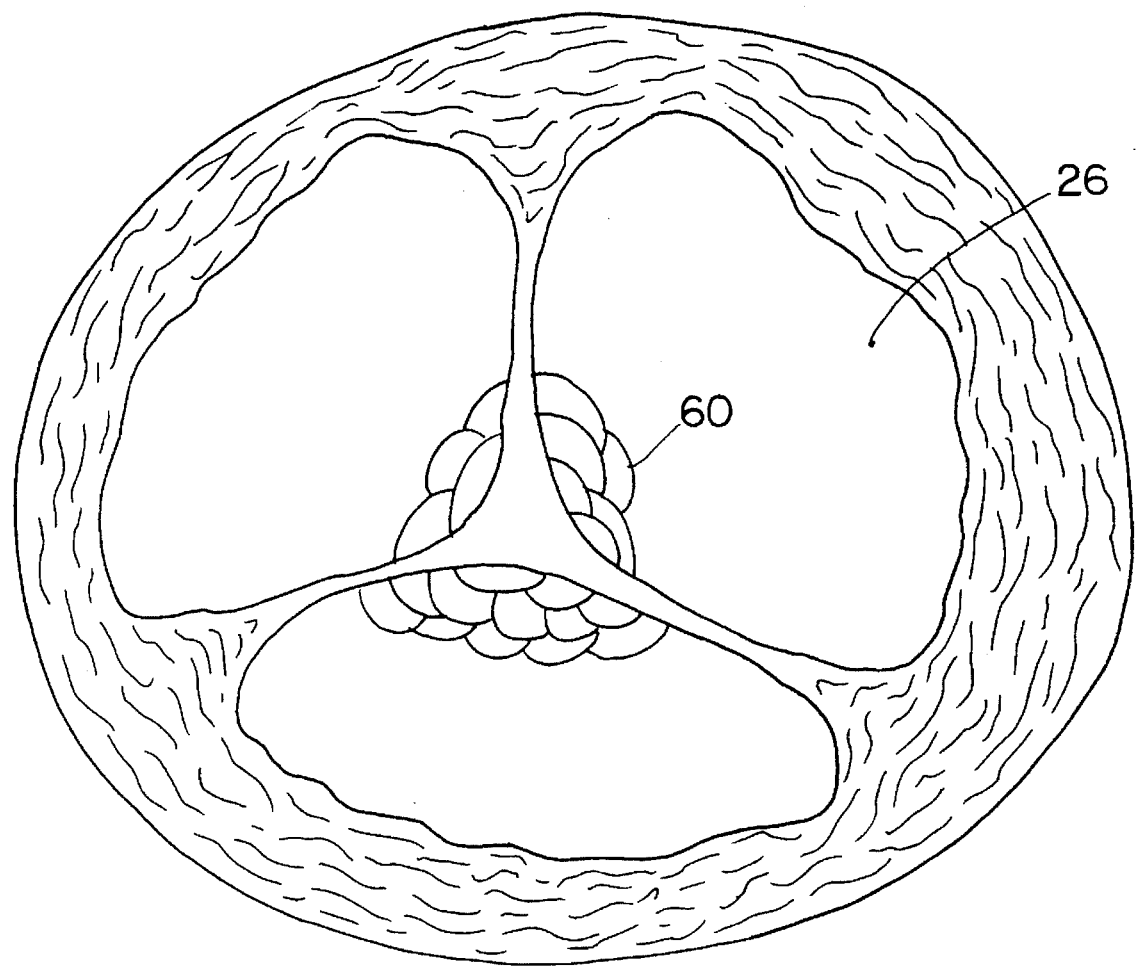
FIG. 7 is an endoscopic view of a prostate with tissue excised.

FIG. 7 is an endoscopic view of a prostate after completion of surgery. Tissue 26 is systematically vaporized along the length of the prostate, widening the prostate canal. Crescent shaped regions 60 remain in the tissue 26 where tissue has been vaporized.

A typical prostate urethra has a diameter on the order of 4–6 mm when not dilated. A preferred diameter for the fiber optics is approximately 0.5 to 1.0 mm while a preferred outer diameter of a bulbous tip at its widest point is approximately 5.0 mm.

The term "fiber optics" as used herein includes a single fiber or a bundle of fibers. Typically, a single optical fiber has a diameter ranging between 0.5 and 1.5 mm. Preferred fiber optics comprise quartz fibers having thin reflective cladding layers, which promote longitudinal propagation of laser light.

The bulbous light delivery tip preferably comprises silica. Other heat absorbing materials, for example metal, may be used. The bulbous tip preferably comprises a refractory material such that it withstands high temperatures. The material is preferably capable of withstanding a range of temperatures from 100° C., the vaporization temperature of tissue, up to 800° C. for absorbing laser radiation.

The thickness of the bulbous tip is not easily controllable, and preferably ranges from 0.05 mm to 0.5 mm for the hollow bulbs of FIG. 4 and FIG. 5. The front face of the tip may be thicker than the body of the tip as shown in FIG. 4, up to 2 mm which may create a lens effect.

The laser source preferably comprises a laser from the following group: Nd:YAG (1.06 μm and 1.44 μm); Ho:YAG (2.10 μm); Tm:YAG (1.94 μm); and diode lasers (800 nm–1 μm). The source is preferably capable of providing power output ranging from 10 W to 100 W in continuous wave or pulsed operation.

The described application of the present invention in endoscopic prostate surgery is intended as an illustration and is not intended as a limitation. The present invention is useful in many other applications where extraction of tissue is required, endoscopic or otherwise.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A surgical laser probe comprising:

fiber optics having an input end and an output end for conveying light;

a laser light source optically coupled to the input end of the fiber optics for providing a laser beam conveyed by the fiber optics of sufficient intensity to vaporize and cause charring of tissue in the laser beam path; and a bulbous, hollow tip member of refractory material, transparent to light at the laser source wavelength, coupled to the output end of the fiber optics, the laser beam being directed toward tissue for vaporizing the tissue with light energy, causing charring of the tissue, the tip member providing a surface surrounding the output end of the fiber optics whereon the vaporized charred tissue collects, the charred tissue absorbing light energy reflected from the tissue causing heating on the tip member for vaporizing the tissue proximate to the tip member with thermal energy, the laser beam being of sufficient intensity to maintain continued vaporization of tissue with light energy as charred tissue collects on the surface of the tip member.

2. The surgical laser probe of claim 1, wherein the tip includes a hole for retaining the output end of the fiber optics.

3. The surgical laser probe of claim 2, wherein the diameter of the fiber optics is substantially similar to the diameter of the hole, providing a snug fit for retaining the fiber optics in the tip.

4. The surgical laser probe of claim 2, wherein the output end of the fiber optics is fused to the hole for retaining the fiber optics in the tip.

5. The surgical laser probe of claim 2 wherein the hole is formed in an extension adapted to retain the fiber optics in the hole in a recessed position so that contact between the output end of the fiber optics and tissue is avoided.

6. The surgical laser probe of claim 1, wherein the tip is substantially solid having a hole along its length for retaining the output end of the fiber optics.

7. The surgical laser probe of claim 6, wherein the diameter of the fiber optics is substantially similar to the diameter of the hole, providing a snug fit for retaining the fiber optics in the tip.

8. The surgical laser probe of claim 6, wherein the output end of the fiber optics is fused to the hole for retaining the fiber optics in the tip.

9. The surgical laser probe of claim 1 wherein the tip comprises silica.

10. The surgical laser probe of claim 1 wherein the surface of the tip member is less than approximately four millimeters from the output end of the fiber optics.

11. A method of performing surgery comprising:

coupling a laser light source to fiber optics, the fiber optics having an input end and an output end;

coupling a bulboust, hollow tip member of refractory material transparent to light at the laser source wavelength to the output end of the fiber optics;

conveying a laser beam from the laser light source through the fiber optics and tip, the laser beam being of sufficient intensity to vaporize and cause charring of tissue in the laser beam path;

directing the laser beam towards tissue for vaporizing the tissue with light energy, causing charring of the tissue; and collecting vaporized charred tissue on a surface of the tip member, the charred tissue absorbing light energy reflected from the tissue, causing heating on the tip member for vaporizing the tissue proximate to the tip member with thermal energy, the laser beam being of sufficient intensity to maintain continued vaporization of tissue with light energy from the laser beam as charred tissue collects on the surface of the tip member.

12. The method claim 11 further comprising the step of providing a hole on the tip for retaining the output end of the fiber optics.

13. The method of claim 12 further comprising the step of coupling the fiber optics to the tip with a snug fit between the output end of the fiber optics and the hole.

14. The method of claim 12 further comprising the step of fusing the output end of the fiber optics to the hole for retaining the fiber optics within the tip.

15. The method of claim 12 further comprising the step of forming the hole in an extension adapted to retain the fiber optics in the hole in a recessed position such that contact between the output end of the fiber optics and tissue is avoided.

16. The method of claim 11 further comprising the step of forming a substantially solid tip having a hole along its length for retaining the output end of the fiber optics.

17. The method of claim 16, further comprising the step of coupling the fiber optics to the tip with a snug fit between the output end of the fiber optics and the hole.

18. The method of claim 16 further comprising the step of fusing the output end of the fiber optics to the hole, for retaining the fiber optics in the tip.

19. The method of claim 11 further comprising the step of forming the tip member from silica.

20. The method of claim 11 further comprising the step of disposing the output end of the fiber optics within four millimeters from the surface of the tip member.

* * * * *